United States Patent
Haft et al.

(10) Patent No.: US 8,387,445 B2
(45) Date of Patent: Mar. 5, 2013

(54) METHOD AND APPARATUS FOR DETERMINING THE ETHANOL PROPORTION OF THE FUEL IN A MOTOR VEHICLE

(75) Inventors: Gerhard Haft, Obermotzing (DE); Rainer List, Regensburg (DE)

(73) Assignee: Continental Automotive GmbH, Hannover (DE)

( * ) Notice: Subject to any disclaimer, the term of this patent is extended or adjusted under 35 U.S.C. 154(b) by 82 days.

(21) Appl. No.: 13/000,193

(22) PCT Filed: Sep. 4, 2009

(86) PCT No.: PCT/EP2009/061445
§ 371 (c)(1),
(2), (4) Date: Jan. 5, 2011

(87) PCT Pub. No.: WO2010/029018
PCT Pub. Date: Mar. 18, 2010

(65) Prior Publication Data
US 2011/0146388 A1 Jun. 23, 2011

(30) Foreign Application Priority Data
Sep. 11, 2008 (DE) .......................... 10 2008 046 719

(51) Int. Cl.
*G01M 15/04* (2006.01)
(52) U.S. Cl. .................. 73/114.55; 73/23.31; 73/114.38
(58) Field of Classification Search ............... 73/23.31, 73/114.38, 114.55; 123/1 A
See application file for complete search history.

(56) References Cited

U.S. PATENT DOCUMENTS

| 4,059,411 | A | 11/1977 | Smith ............................... 44/51 |
| 5,197,451 | A | 3/1993 | Yoshida et al. ............... 123/696 |
| 5,950,599 | A * | 9/1999 | Rotramel et al. ............. 123/436 |
| 6,206,940 | B1 | 3/2001 | Weissman et al. .............. 44/449 |
| 6,257,174 | B1 | 7/2001 | Huff et al. ..................... 123/1 A |

(Continued)

FOREIGN PATENT DOCUMENTS

| DE | 10257686 A1 | 7/2004 |
| DE | 60011393 T2 | 6/2005 |

(Continued)

OTHER PUBLICATIONS

German Office Action, German patent application No. 10 2008 046 719.7-26, 3 pages, Jun. 16, 2009.
International PCT Search Report, PCT/EP2009/061445, 12 pages, Oct. 7, 2009.

*Primary Examiner* — Freddie Kirkland, III
(74) *Attorney, Agent, or Firm* — King & Spalding L.L.P.

(57) ABSTRACT

Internal combustion engines which are operated using ethanol exhibit an improved capability for lean-burn running. The lean-burn running limit with a higher ethanol proportion is displaced in the direction of lean. This link between the lean-burn running limit and the ethanol proportion of the fuel is used to determine the ethanol proportion. To determine the lean-burn running limit, a fuel quantity is injected into a cylinder in the operating range of the overrun fuel cut-off, with which fuel quantity no combustion of the air/fuel mixture occurs, and the fuel quantity is increased continuously until combustion occurs; the smooth running of the engine is monitored for this cylinder and the lean-burn running limit is detected as reached if the smooth running exceeds a predefined threshold value. The ethanol proportion is then deduced from the increase in the injected fuel quantity which is required to reach the lean-burn running limit.

10 Claims, 3 Drawing Sheets

U.S. PATENT DOCUMENTS

| | | | |
|---|---|---|---|
| 6,298,838 B1 | 10/2001 | Huff et al. ................. 123/674 |
| 6,714,856 B2 * | 3/2004 | Huff et al. ................. 701/114 |
| 7,523,723 B2 * | 4/2009 | Marriott et al. ............ 123/1 A |
| 8,113,174 B2 * | 2/2012 | Haft et al. ................. 123/436 |
| 2006/0047405 A1 | 3/2006 | Bouchain et al. .......... 701/104 |
| 2008/0035119 A1 * | 2/2008 | Marriott et al. ............ 123/494 |
| 2009/0308350 A1 | 12/2009 | Haft et al. ................. 123/436 |

FOREIGN PATENT DOCUMENTS

| | | |
|---|---|---|
| DE | 102006043341 A1 | 3/2008 |
| JP | 3217644 A | 9/1991 |

* cited by examiner

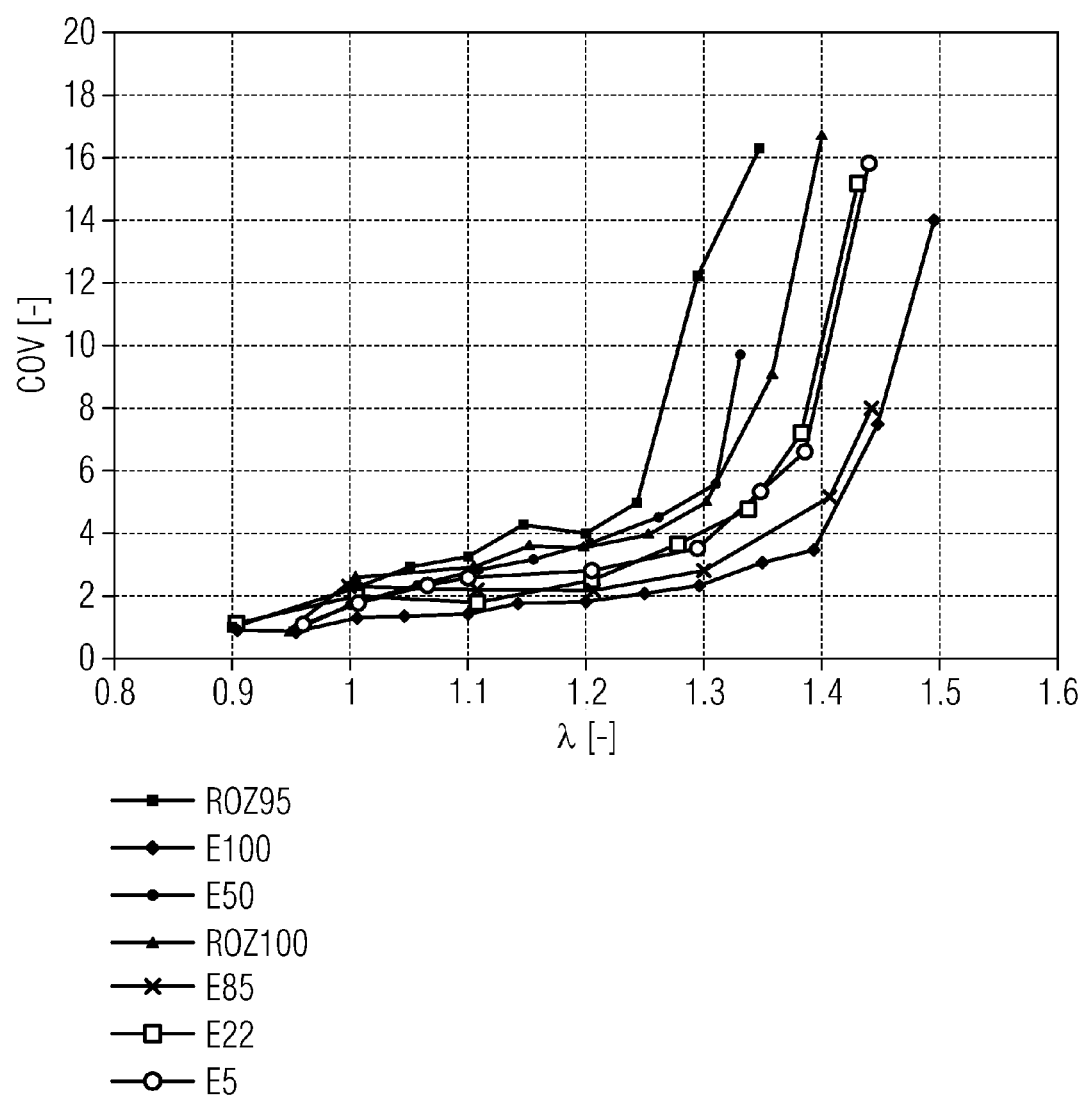

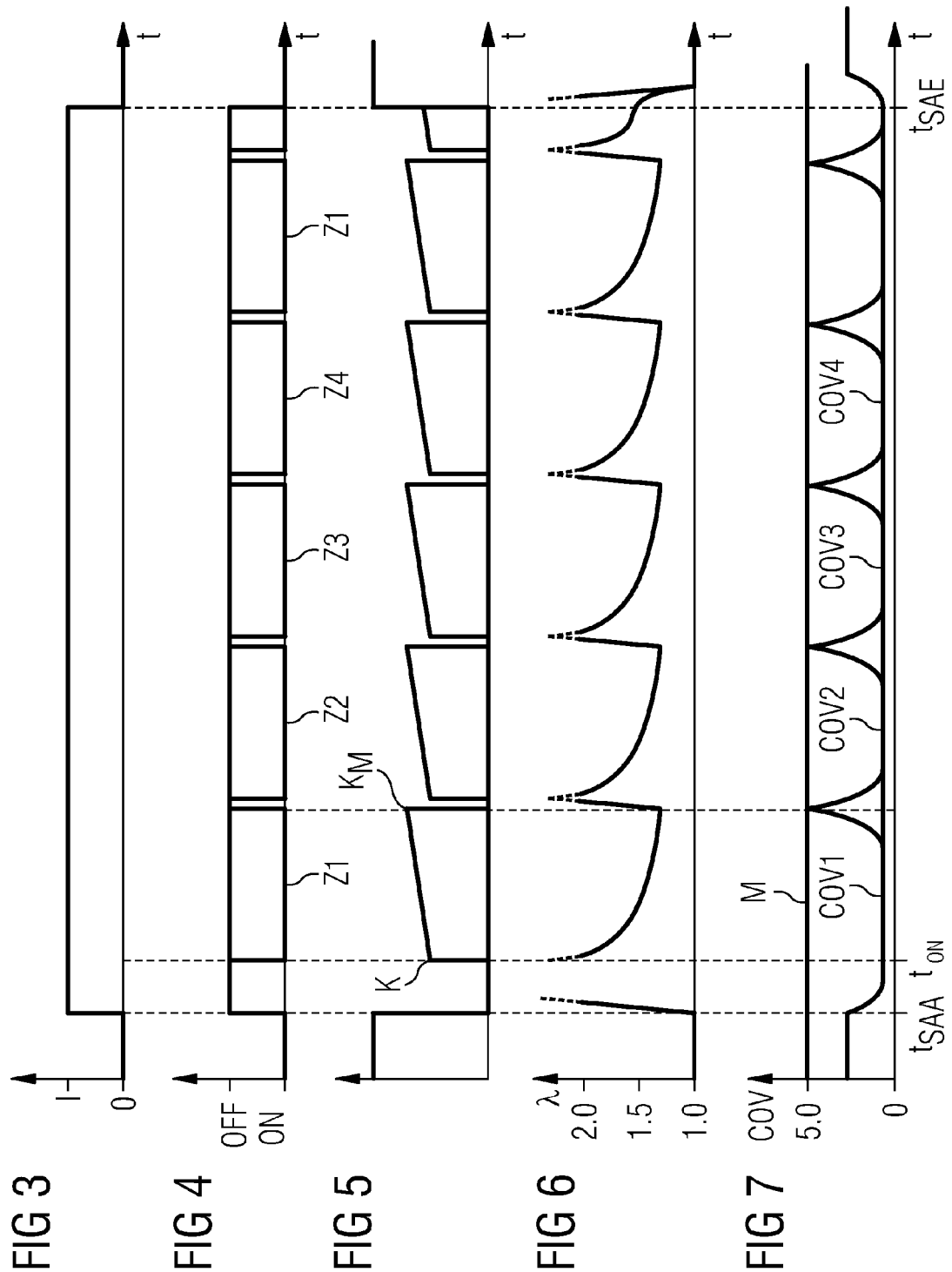

METHOD AND APPARATUS FOR DETERMINING THE ETHANOL PROPORTION OF THE FUEL IN A MOTOR VEHICLE

CROSS-REFERENCE TO RELATED APPLICATIONS

This application is a U.S. National Stage Application of International Application No. PCT/EP2009/061445 filed Sep. 4, 2009, which designates the United States of America, and claims priority to German Application No. 10 2008 046 719.7 filed Sep. 11, 2008, the contents of which are hereby incorporated by reference in their entirety.

TECHNICAL FIELD

The present invention relates to a method and an apparatus for determining the ethanol proportion of the fuel in a motor vehicle.

BACKGROUND

The operation of motor vehicles using fuel that contains ethanol (alcohol) is already tried and tested, and, primarily in South America and North America, many vehicles are equipped for this type of operation. The concentration of the ethanol in the tank fuel can change from one tank filling to the next tank filling, depending on the fuel type that is added. Arbitrary ethanol proportions of the fuel between 0% and 100% can be produced in this context. In order to achieve perfect running of the internal combustion engine, it is necessary for the operating control device to detect the new fuel composition as soon as possible and take this into consideration as part of its control strategies.

The prior art (see e.g. U.S. Pat. No. 6,257,174 B1) already discloses the use of the different air requirement of ethanol as opposed to other fuels (ethanol: 8.9; gasoline: 14.7) for determining the ethanol proportion of the fuel. If the ethanol proportion of the fuel changes, the air ratio $\lambda$ that is measured by the $\lambda$ sensor changes, and the ethanol proportion of the fuel can be deduced from this change in the air ratio ($\lambda$ method).

However, the $\lambda$ method only allows the ethanol proportion to be reliably determined in the case of a fuel system that is intact. Since the fuel system diagnosis (FSD) is also carried out using the $\lambda$ values that are measured by the $\lambda$ sensor, the $\lambda$ method does not provide reliable values. Specifically, the operating control device cannot definitively establish whether a deviation of the $\lambda$ value is caused by a changed ethanol proportion of the fuel or an error in the fuel system.

U.S. Pat. No. 6,298,838 B1 discloses a method for controlling the irregular running of the engine, in which method the ethanol content of the fuel supplied to the engine is varied. Provision is made to measure an irregular running of the engine, and for the fuel supply to the engine to be increased by a first ethanol content if a first threshold value is exceeded. The irregular running is then measured again. If the irregular running has been reduced below the first threshold value as a result of this ethanol increase, but remains above a second, lower threshold value, the fuel supplied to the engine is further increased by a second ethanol proportion, in order to bring the irregular running below the second threshold value as well. However, if no reduction in the irregular running below the first threshold value is established as a result of increasing the fuel by the first ethanol proportion, it is deduced that the irregular running is not caused by a decrease in the ethanol proportion, but has another reason, for example a defective spark plug.

The publications DE 600 11 393 T2 and U.S. Pat. No. 4,059,411 A propose fuel compositions whose alcohol content is increased in order to extend the lean-burn running limit of the engine.

SUMMARY

According to various embodiments, a method for determining the ethanol proportion of the fuel of a motor vehicle can be specified, which method is not dependent on a measurement of the air ratio $\lambda$ in the exhaust gas of the internal combustion engine.

According to an embodiment, in a method for determining the ethanol proportion of the fuel for an internal combustion engine of a motor vehicle, wherein the dependency of the lean-burn running limit of the internal combustion engine of the motor vehicle on the ethanol proportion of the fuel is used for determining the ethanol proportions, for the purpose of determining the lean-burn running limit, a fuel quantity is injected into a cylinder of the internal combustion engine in the operating range of the overrun fuel cutoff of the internal combustion engine, with which fuel quantity no combustion of the air/fuel mixture occurs, the fuel quantity is progressively increased until combustion occurs, the smooth running of the internal combustion engine is monitored during this activity for this cylinder, and the lean-burn running limit is recognized as having been reached when the smooth running exceeds a predefined threshold value, wherein the ethanol proportion of the fuel is then deduced from the increase in the injected fuel quantity which is required to reach the lean-burn running limit.

According to a further embodiment, the ethanol proportion of the fuel can be obtained from a characteristic map, in which the ethanol proportion is plotted over the increase in the injected fuel that is required to reach the lean-burn running limit. According to a further embodiment, the ethanol proportion in the characteristic map can be plotted depending on rotational speed and load of the internal combustion engine. According to a further embodiment, the determining of the ethanol proportion of the fuel can be used to validate the ethanol proportion that was obtained by means of another method.

According to another embodiment, in an apparatus for determining the ethanol proportion of the fuel for an internal combustion engine of a motor vehicle, the apparatus may execute the method as described above.

BRIEF DESCRIPTION OF THE DRAWINGS

Further embodiments and developments are explained below in conjunction with the description of the exemplary embodiment, wherein:

FIG. 2 shows a diagram which illustrates the smooth-running value COV over the air ratio $\lambda$, FIG. 3 shows a diagram which illustrates the temporal profile of an overrun fuel cutoff phase, FIG. 4 shows a diagram which illustrates the connection of the individual cylinders during the overrun fuel cutoff phase, FIG. 5 shows a diagram which illustrates the injected fuel quantity over time t, FIG. 6 shows a diagram which illustrates the air ratio $\lambda$ over time t, and FIG. 7 shows a diagram which illustrates the smooth-running value COV over time t.

DETAILED DESCRIPTION

Figure 1:
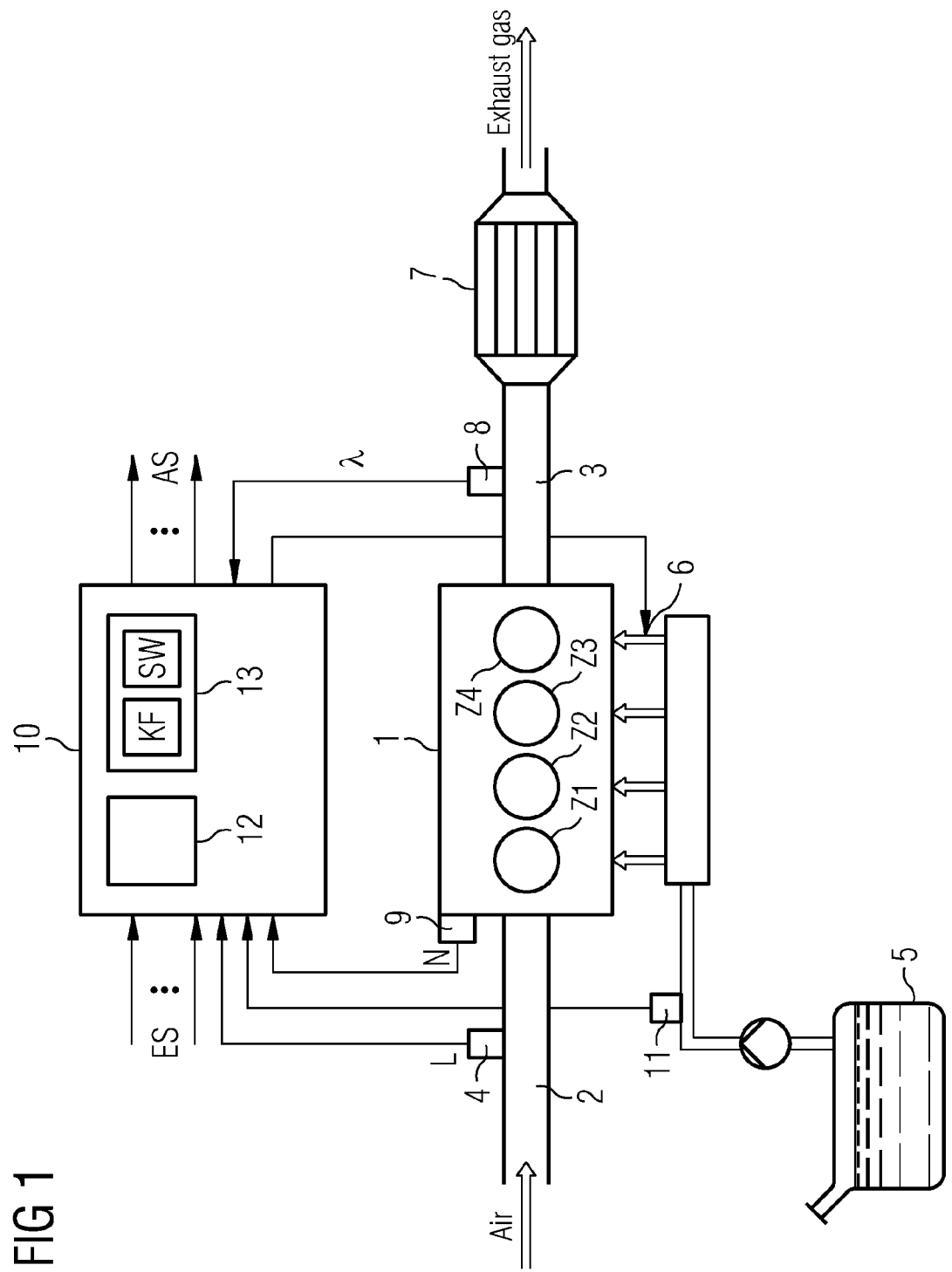
FIG. 1 schematically shows a block diagram of an internal combustion engine with an associated electronic control unit.

The various embodiments are based on the finding that internal combustion engines which are operated using ethanol exhibit an improved capability for lean-burn running. That is to say, the lean-burn running limit of the internal combustion engine is moved in the direction of lean by virtue of a higher ethanol proportion of the fuel. This relationship between lean-burn running limit and ethanol proportion of the fuel is used for determining the ethanol proportion.

For the purpose of determining the lean-burn running limit, a fuel quantity is injected into a cylinder of the internal combustion engine in the operating range of the overrun fuel cutoff of the internal combustion engine, with which fuel quantity no combustion of the air/fuel mixture occurs, and the fuel quantity is progressively increased until combustion occurs, whereby during this activity, the smooth running of the internal combustion engine is monitored for this cylinder and the lean-burn running limit is recognized as having been reached when the smooth running exceeds a predefined threshold value. The ethanol proportion of the fuel is then deduced from the increase in the injected fuel quantity which is required to reach the lean-burn running limit.

By injecting fuel into only one cylinder and cutting off the fuel injection of the remaining cylinders during the overrun fuel cutoff, these cylinders do not influence the smooth-running values of the internal combustion engine. The ethanol content can therefore be determined reliably and accurately.

Since the determining of the ethanol content of the fuel takes place during the overrun fuel cutoff phase, it is not necessary to disable any other functions such as for example tank venting or lambda adjustment.

According to an development, the ethanol proportion of the fuel is obtained from a characteristic map, in which the ethanol proportion is plotted over the increase in the injected fuel which is required to reach the lean-burn running limit. This has the advantage of being particularly easy to perform.

The method according to various embodiments is used in particular to validate the ethanol proportion which is obtained by means of a different method (in particular the λ method).

Furthermore, the method according to various embodiments makes it possible to validate the signal of a fuel sensor, in particular an ethanol sensor, which is arranged in the fuel circuit of the internal combustion engine.

The reliability when determining the ethanol proportion can therefore be increased in a simple manner.

FIG. 1 shows a schematic illustration of an internal combustion engine 1 of a motor vehicle which can be operated using both gasoline and alcohol, or using any mixing ratio of these fuels. Such motor vehicles are referred to as flexible fueled vehicle (FFV) or variable fuel vehicles (VFV). Only the components required to understand the various embodiments are illustrated in this figure. The various embodiments are explained with reference to an internal combustion engine comprising 4 cylinders Z1-Z4, though it can also be applied to internal combustion engines having a different number of cylinders and is actually independent of the type of engine design, e.g. four-stroke gasoline engines, two-stroke engines, reciprocating-piston engines or rotating-piston engines.

The internal combustion engine 1 is assigned an intake section 2 and an exhaust-gas section 3, these being connected to the combustion chambers of the cylinders Z1-Z4 of the internal combustion engine 1 by means of inlet valves and outlet valves. The fresh air which is required for combustion of the fuel/air mixture is supplied to the internal combustion engine 1 via the intake section 2. Provision is made in the intake section 2, inter alia, for a load sensor 4. For example, an air mass meter or an induction pipe sensor can be provided as a load sensor 4. The signal of the load sensor 4 is identified by the reference sign L. The fuel or fuel mixture required for combustion is taken from a fuel storage container 5 and supplied to the injection valves 6 that are assigned to the individual cylinders Z1 to Z4. The fuel can be injected into the individual induction pipes of the cylinders or directly into the combustion chambers of the corresponding cylinders (direct fuel injection).

After combustion, the exhaust gas flows via the exhaust-gas section 3, an exhaust-gas catalytic converter 7 and a muffler (not shown) into the environment in a cleaned state.

Upstream of the exhaust-gas catalytic converter 7, provision is made for an exhaust-gas sensor 8, which preferably takes the form of a lambda sensor and which captures a residual oxygen content in the exhaust gas and emits a corresponding signal λ. The internal combustion engine 1 is additionally assigned a rotational speed sensor 9, which emits a signal that corresponds to the rotational speed N of the crankshaft of the internal combustion engine. In an embodiment, the fuel circuit has a sensor 11 which captures the fuel composition, i.e. the proportion of ethanol in the fuel.

For the purpose of controlling and regulating the internal combustion engine 1, an electronic control unit (ECU) 10 is provided which, in addition to the aforementioned sensors, is assigned further sensors that are required for the operation of the internal combustion engine 1, wherein said further sensors are not explicitly illustrated in the figure and the signals they supply are indicated generally in the figure by means of the reference sign ES. The sensors capture various measured variables and determine the measured value of the measured variable in each case. Depending on at least one of the measured variables, the electronic control unit 10 determines actuating variables which are then converted into one or more actuating signals for controlling the actuators by means of corresponding servomechanisms.

The actuators include for example a throttle valve in the intake section and the injection valves 6. Further signals for further actuators, which are required for operating the internal combustion engine 1 but are not shown explicitly, are identified generally in the figure by means of the reference sign AS.

A plurality of engine control functions that are based on characteristic maps are implemented by means of software in the electronic control unit 10. In particular, the electronic control unit 10 determines the appropriate ignition timing and the injection duration as a function of the load signal L and the rotational speed N, taking into consideration the composition of the flex-fuel. Also implemented in the electronic control unit 10 is what is known as an overrun fuel cutoff function 12. Overrun fuel cutoff is understood to mean the complete interruption of the fuel inflow to the internal combustion engine during overrun operation. The overrun operating mode is a load state in which negative work is performed, i.e. the internal combustion engine does not deliver energy but absorbs energy. Overrun operating mode occurs in a gasoline engine when the throttle valve is suddenly closed and the rotational speed of the internal combustion engine is greater than the idle speed, such that the vehicle mass is slowed down by the absorption of energy.

The electronic control unit 10 is assigned a data memory 13, in which are stored, inter alia, characteristic maps KF and threshold values SW, the significance of these being further explained with reference to the following figures.

As mentioned above, the various embodiments take advantage of the fact that the capability for lean-burn running of the internal combustion engine improves as the ethanol proportion of the fuel increases. This relationship is evident in the diagram in FIG. 2, in which the smooth-running value COV (coefficient of variance) is plotted over the air ratio λ for various fuels. The dimensionless smooth-running value COV characterizes the irregular running of an internal combustion engine; i.e. the irregular running increases as the smooth-running value COV increases. A predefined threshold value (for example COV=5) is defined as a lean-burn running limit, above which acceptable smooth running of the internal combustion engine no longer occurs.

The curves ROZ95 and ROZ100 shown in the diagram in FIG. 2 apply to pure gasoline having a research octane number of 95 and 100, while the curves E5, E50, E85 and E100 apply to fuels having an ethanol proportion of 5%, 50%, 85% and 100% respectively.

It can be seen from the diagram in FIG. 2 that the lean-burn running limit (COV=5) moves in the direction of a larger air ratio λ (i.e. in the direction of lean) as the ethanol proportion of the fuel increases. For example, the lean-burn running limit for gasoline ROZ95 has a λ value of approximately 1.25, while the lean-burn running limit for a pure ethanol (E100) has λ value of approximately 1.42.

On the basis of the diagrams in the FIGS. 3 to 7, the method is now explained in greater detail with reference to a four-cylinder internal combustion engine as illustrated in FIG. 1, for example.

The overrun fuel cutoff function 12, as implemented in the electronic control unit 10, is activated at a time point $t_{SAE}$. The opening angle of a throttle valve that is arranged in the intake section and the momentary rotational speed N of the internal combustion engine 1, for example, can be used as a criterion for this, and these two parameters can be related to each other in a known manner. The fuel supply for all cylinders Z1-Z4 is enabled ("ON" state in FIG. 4) until the time point $t_{SAA}$, and the logical signal for overrun fuel cutoff is at level 0 (FIG. 3). At the time point $t_{SAA}$, the logical signal for overrun fuel cutoff switches to level 1 and the fuel supply for all cylinders Z1-Z4 is disabled ("OFF" state in FIG. 4). In a conventional overrun fuel cutoff function, this disconnection of the fuel supply remains in effect for all cylinders until the time point $t_{SAE}$.

According to various embodiments, at the time point $t_{ON}$, the fuel supply for the cylinder Z1 is enabled while remaining disabled for the other cylinders Z2-Z4. Starting from a value for the injection quantity, with which no combustion of the air/fuel mixture yet occurs (very lean mixture with an air ratio of e.g. λ=2), the fuel quantity is progressively increased. This is illustrated in FIG. 5 with the aid of a factor K for the fuel quantity that is to be injected.

At the same time as the described change in the injected fuel quantity, the smooth running of the internal combustion engine is monitored for this cylinder Z1. Since the monitoring of the smooth running is known from the prior art (cf. e.g. DE 41 22 139 and DE 197 41 965), this is not described in greater detail here. As shown in FIG. 7, the smooth-running value COV1 for the first cylinder Z1 becomes gradually larger (FIG. 7) as the injected fuel quantity continuously increases and the air/fuel mixture becomes richer accordingly (air ratio λ decreases from the value 2.0 as per FIG. 6).

In the exemplary embodiment here, the COV value of 5 has been assumed, representing the lean-burn running limit M. The reference sign $K_M$ in FIG. 5 designates the factor for the increase in the fuel quantity that causes the smooth-running value COV1 for the first cylinder Z1 to reach the lean-burn running limit M (COV=5, FIG. 7). This factor, which is assigned to the lean-burn running limit M, now allows the ethanol proportion of the fuel to be determined.

The ethanol proportion is appropriately read out from a characteristic map KF of the electronic control unit 10, in which map the ethanol proportion is plotted over the factor $K_M$. For practical reasons, it can also be appropriate to plot the ethanol proportion over $\lambda_M$ in the characteristic map, where $\lambda_M=1/K_M$.

When the smooth-running value COV1 for the first cylinder has reached the lean-burn running limit M, the increase in the fuel quantity to be injected for the first cylinder Z1 is halted. The described method for increasing the injected fuel quantity is then performed for the remaining cylinders Z2-Z4 in turn, as indicated in the diagrams in FIGS. 4-7. The smooth-running values for these cylinders are designated by COV2 to COV4 in FIG. 7. The ethanol proportion of the fuel is then finally determined from a statistical analysis of the results for all cylinders and by means of a plurality of passes through the described method.

As already described in the introduction, the ethanol proportion of the fuel determined in this way can be used to validate the ethanol proportion which is obtained by means of a different method. An essential advantage of the method according to various embodiments is that it does not depend on a measurement of the λ value. By virtue of this validation, it is therefore possible to establish whether a change in the λ value is due to a change in the ethanol proportion or an error of the fuel system. Using the validated values of the λ method, the operating control device can then perform the λ adjustment method which is already known and hence the fuel system diagnosis (FSD).

What is claimed is:

1. A method for determining an ethanol proportion of a fuel for an internal combustion engine of a motor vehicle, wherein a dependency of a lean-burn running limit of the internal combustion engine of the motor vehicle on the ethanol proportion of the fuel is used for determining the ethanol proportions, the method comprising: for the purpose of determining the lean-burn running limit, injecting a first fuel quantity into a cylinder of the internal combustion engine in an operating range of an overrun fuel cutoff of the internal combustion engine, the first fuel quantity insufficient to allow combustion of the air/fuel mixture, increasing the fuel quantity progressively until combustion occurs, monitoring a smooth running of the internal combustion engine during this activity for this cylinder, and recognizing the lean-burn running limit as having been reached when the smooth running exceeds a predefined threshold value, wherein the ethanol proportion of the fuel is then deduced from the increase in the injected fuel quantity which is required to reach the lean-burn running limit.

2. The method according to claim 1, wherein the ethanol proportion of the fuel is obtained from a characteristic map, in which the ethanol proportion is plotted over the increase in the injected fuel that is required to reach the lean-burn running limit.

3. The method according to claim 2, wherein the ethanol proportion in the characteristic map is plotted depending on rotational speed and load of the internal combustion engine.

4. The method according to claim 1, wherein the determining of the ethanol proportion of the fuel is used to validate the ethanol proportion that was obtained by means of another method.

5. An apparatus for determining an ethanol proportion of a fuel for an internal combustion engine of a motor vehicle, wherein the apparatus is configured to cause:
- an injection of a first fuel quantity into a cylinder of the internal combustion engine in an operating range of an overrun fuel cutoff of the internal combustion engine, the first fuel quantity insufficient to allow combustion of the air/fuel mixture,
- a progressive increase of the fuel quantity until combustion occurs,
- a monitoring of a smooth running of the internal combustion engine during this activity for this cylinder, and
- a recognition of a lean-burn running limit as having been reached when the smooth running exceeds a predefined threshold value, wherein the ethanol proportion of the fuel is then deduced from the increase in the injected fuel quantity which is required to reach the lean-burn running limit.

6. The apparatus according to claim 5, wherein the ethanol proportion of the fuel is obtained from a characteristic map, in which the ethanol proportion is plotted over the increase in the injected fuel that is required to reach the lean-burn running limit.

7. The apparatus according to claim 6, wherein the ethanol proportion in the characteristic map is plotted depending on rotational speed and load of the internal combustion engine.

8. The apparatus according to claim 5, wherein the determining of the ethanol proportion of the fuel is used to validate the ethanol proportion that was obtained by means of another method.

9. A motor vehicle comprising an electronic control unit for determining an ethanol proportion of a fuel for an internal combustion engine of the motor vehicle, wherein a dependency of a lean-burn running limit of the internal combustion engine of the motor vehicle on the ethanol proportion of the fuel is used for determining the ethanol proportions, the electronic control unit being configured,
for the purpose of determining the lean-burn running limit, to inject a first fuel quantity into a cylinder of the internal combustion engine in an operating range of an overrun fuel cutoff of the internal combustion engine, the first fuel quantity insufficient to allow combustion of the air/fuel mixture, to increase the fuel quantity progressively until combustion occurs, to monitor a smooth running of the internal combustion engine during this activity for this cylinder, and to recognize the lean-burn running limit as having been reached when the smooth running exceeds a predefined threshold value, wherein the ethanol proportion of the fuel is then deduced from the increase in the injected fuel quantity which is required to reach the lean-burn running limit.

10. The motor vehicle according to claim 9, wherein the ethanol proportion of the fuel is obtained from a characteristic map, in which the ethanol proportion is plotted over the increase in the injected fuel that is required to reach the lean-burn running limit.

* * * * *